United States Patent [19]

Jachowicz et al.

[11] Patent Number: 4,588,760
[45] Date of Patent: May 13, 1986

[54] HAIR TREATMENT COMPOSITION

[75] Inventors: Janusz Jachowicz; Leszek J. Wolfram, both of Stamford, Conn.

[73] Assignee: Clairol Incorporated, New York, N.Y.

[21] Appl. No.: 764,025

[22] Filed: Aug. 9, 1985

[51] Int. Cl.$^4$ .......................... A45D 7/04; A61K 7/09; C08G 14/06
[52] U.S. Cl. ............................................ 524/12; 132/7; 8/127.5; 8/127.51; 8/127.6; 8/128 R; 8/128 A; 424/71; 528/162; 528/163
[58] Field of Search ................................ 524/12; 132/7; 8/115.51, 127.5, 127.51, 127.6, 128 R, 128 A; 546/82; 424/71

[56] References Cited

U.S. PATENT DOCUMENTS

| | | | |
|---|---|---|---|
| 2,749,342 | 6/1956 | Auchincloss | 544/186 |
| 3,228,829 | 1/1966 | Wolf et al. | 514/244 |
| 3,244,710 | 4/1966 | Larsen | 544/185 |
| 3,760,819 | 9/1973 | Vogt | 424/71 |
| 4,069,220 | 1/1978 | Orem et al. | 544/186 |
| 4,338,295 | 7/1982 | Highly et al. | 424/71 |

Primary Examiner—John Kight
Assistant Examiner—Nathan M. Nutter
Attorney, Agent, or Firm—Gabriel P. Katona

[57] ABSTRACT

Method and composition for modifying moisture retention of hair and thus improving its settability which comprises applying to hair an aqueous solution containing a heximinium salt and a resorcinol under conditions promoting in situ polymerization.

14 Claims, No Drawings

HAIR TREATMENT COMPOSITION

FIELD OF THE INVENTION

The field of invention concerns broadly the treatment of natural and artificially produced protein fibers to form and deposit within the fibers a polycondensation reaction product polymer of a heximinium salt and a resorcinol. The treated protein fibers include natural fibers such as human hair, animal hair, wool and silk, and artificial fibers such as those spun from soybean protein, casein, zein or gelatin solutions.

The field of invention particularly concerns the treatment of human hair on the head, to decrease the hygroscopicity of hair and thus to improve the stiffness and impart settability to the hair such that a desired hair set can be maintained. Such treatments include curling, setting, permanent waving, straightening and repair of damaged hair.

DESCRIPTION OF THE PRIOR ART

The most commonly used method of altering the natural configuration of hair is to wet it with water, arrange the hair in the desired configuration, allow the hair to dry and comb it into a desired style. This practice is satisfactory for the purpose of temporarily altering natural hair styles, but does not provide a method of altering hair style without the need for daily water setting. Further, in the presence of moisture, for example, on a damp day, the water set hair will tend to return to its original configuration. Clearly a modification of hair whereby its moisture receptivity would be decreased would be of great value to hair styling in general and to style retention in particular.

The need for improved style retention has been recognized as seen by recent attempts to utilize polymer chemistry to permanently alter the water setting behavior of keratin fibers. It has been proposed that keratin fibers, including hair, be treated with a variety of monomeric compounds under conditions such that the monomers can penetrate into the fiber structure before undergoing polymerization. Depending on the amount of polymer formed in situ, the resulting fiber should have properties related to both unmodified keratin fiber and a fiber composed entirely of the synthetic polymer.

The more recent work appears to have been directed to efforts to develop ways to use various vinyl polymers in addition to polymerization processes. Earlier work involved the condensation polymerization of hydroxyaromatic compounds with aldehydes, primarily formaldehyde. These systems while capable of imparting to hair improved settability, have not been successful notably because of the unacceptability of formaldehyde and the harsh feel the hair is left with after treatment owing to polymeric surface deposits.

The Vogt U.S. Pat. No. 3,760,819 discloses a method for permanently waving hair which comprises applying to the hair a solution containing ammonium thioglycolate hair softening agent and a quaternary ammonium halide salt alkylating agent for the hair. Patentee discloses as suitable alkylating agents the bis-hexamethylene tetramine salt of 1.4-dichloro 2-butene and the bis-hexamethylenetetramine salt of para-bis-chloromethylbenzene.

The Breuer U.S. Pat. No. 4,278,659 discloses a method of imparting shampoo resistant body and settability to hair comprising the application to hair of an aqueous solution containing a precondensate of glyceraldehyde and resorcinol under condition promoting in situ polymerization in the hair fiber.

The Oren et al U.S. Pat. No. 4,069,220 broadly discloses that complexes of resorcinol and hexamethylenetetramine can be prepared by combining a solution of resorcinol with a solution of the hexamethylenetetramine. When the two solutions are combined a solid is precipitated. The precipitate may be filtered and dried to give a product known as resotropin. Patentee teaches that the resotropin product may be heated to give resins that are useful in improving the adhesion of rubber to automobile tire cords.

The following additional patents may be of interest.

Highley et al U.S. Pat. No. 4,338,295, Hair Setting and Bodying Compositions and Method.

Bresak et al U.S. Pat. No. 4,452,261, Hair Setting and Method.

Hart U.S. Pat. No. 4,014,827, Substrate Reinforced Rubber Structure and Compound For Forming Same.

SUMMARY OF THE INVENTION

In accordance with the present invention, keratin fibers including hair are treated with an aqueous solution comprising a heximinium salt and resorcinol to obtain in situ deposition of a condensation polymer. The fibers treated in this manner, particularly hair, exhibit improved stiffness and settability. The improved settability imparted to hair is resistant to high humidity and removal by normal shampooing. The treated hair is similar to intact hair in feel, luster, mechanical strength and wet and dry combing characteristics.

DISCUSSION OF THE INVENTION

The heximinium salts used in accordance with the present invention are quaternary ammonium halide salts formed by reacting hexamethylenetetramine with an organic halide. These can be described by the general formula.

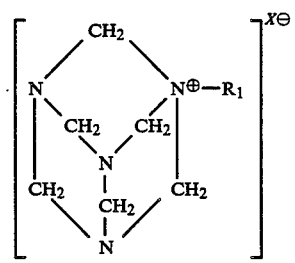

wherein $R_1$ is essentially any organic radical and X is a halide (e.g. Cl, Br, I). This, for example $R_1$ may be substituted or unsubstituted straight chain or branched chain alkyl, aryl, aralkyl or olefinic radicals. The substituents that these radicals may carry are varied and are exemplified by such groups as the halogens e.g. Cl, Br, I, hydroxy groups etc. As a practical matter $R_1$ will rarely exceed 18 carbon atoms and will preferably contain from 2-18 carbon atoms.

Since the process of the present invention will usually be carried using essentially aqueous compositions this will place a limit on the heximinium salt that will be utilized. Generally the salt will be selected so that is is water dispersible and preferably water soluble.

By way of further illustration of the heximinium salts that are useful for the present purposes the following may be mentioned:

Suitable heximinium salts are as follows:
Ethylheximinium iodide [$C_6H_{12}N_4C_2H_5$]I,
Ethanolheximinium iodide $C_6H_{12}N_4C_2H_5OH$]I,
Benzylheximinium bromide [$C_6H_{12}N_4CH_2C_6H_5$]Br,
Isopropylheximinium iodide [$C_6H_{12}N_4CH(CH_3)_2$]I,
1-(3-chloro-2-propenyl)heximinium chloride [$C_6H_{12}N_4CH=CHCH_2Cl$]Cl,
tetradecylheximinium iodide [$C_6H_{12}N_4C_{19}H_{29}$]I,
octadecylheximinium bromide [$C_6H_{12}N_4C_{18}H_{37}$]Br
allyl heximinium bromide [$C_6H_{12}N_4CH_2CH=CH_2$]Br The heximinium salts were prepared by dissolving 0.1 mole of heximine (hexamethylenetetramine) in 150 ml. of $CHCl_3$ and adding 0.1 mole of the respective organic halide e.g. ethyl iodide, ethanol iodide, benzyl bromide or isopropyl iodide.

The solutions were refluxed for at least one hour an the reaction mixtures were cooled and left overnight for crystallization. In each case a white crystaline material was filtered off and washed with $CHCl_3$.

The following are exemplary of products that were obtained:

Ethylheximinium iodide, yield 68%, m.p. 153°-154° C. (decomp.);

2-Ethanolheximinium iodide, yield 38%, m.p. 152°-153° C. (decomp.);

Benzylheximinium bromide, yield 96%, m.p. 176°-177° C. (decomp.); and

Isopropylheximinium iodide, yield 11% (after one week reaction), m.p. 146°-147° C. (decomp.)

Tetradecylheximinium iodide, yield 32%, m.p. 168° C. (decomp.)

Octadecylheximinium bromide, yield 36%, m.p. 176° C. (decomp.)

1-(3-chloro-2-propenyl) heximinium chloride (m.p. 183° C., decomp.) is commercially available product sold under the name Quaternium-15 (DoW Chemical).

The corresponding bis-quaternary ammonium salts of hexamethylene tetramine can also be obtained by increasing the molar ratio of organic halide to heximethylene-tetramine from 1:1 to 2:1.

The resorcinol compounds that can be used are resorcinol and substituted resorcinol compounds having the formula:

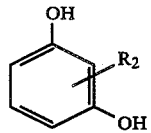

wherein $R_2$ is hydrogen or an alkyl having 1 to 12 carbon atoms, such as methyl, ethyl or propyl group. Suitable resorcinol compounds are resorcinol, methyl resorcinol, ethyl resorcinol, dodecyl resorcinol etc.

The condensation polymerization reaction that occurs in the aqueous solution containing heximinium salt and a resorcinol is as follows:

1. The heximinium salt in water hydrolyzes and decomposes to form primary amine, ammonia and formaldehyde:

The concentration of formaldehyde is maintained very low because it reacts with both the $R_1NH_2$ and $NH_3$ to form intermediate amine products, such as $CH_2=NHR_1$ and $CH_2=NH_2$, which intermediate amine products react with the resorcinol to form the polymer.

2. The condensation polymerization reaction may follow either of two routes:

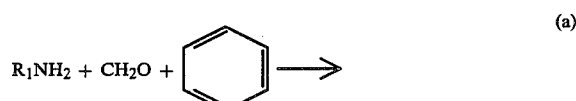

(a)

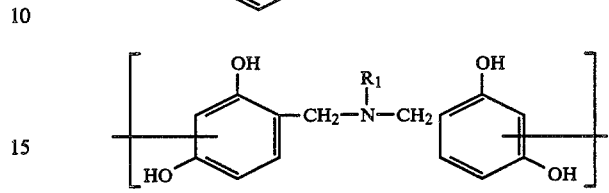

or

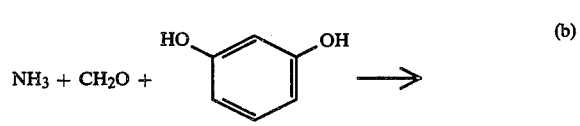

(b)

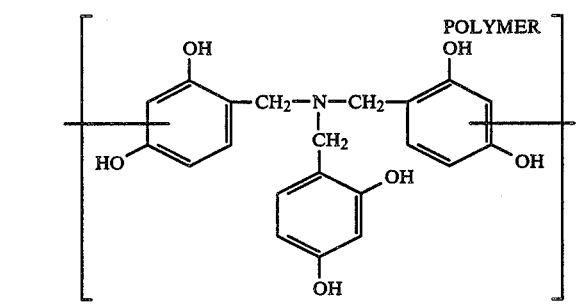

Primary amine $R_1NH_2$ form a linear segment of the polymer chain, while $NH_3$ can serve as a branching point. The analysis of $H^1$-NMR spectra indicates that the resorcinol-heximinium salts polycondensates are highly branched and the content of the primary amine in the polymer structure is relatively small. The polymers obtained at higher concentration of heximinium salt (higher ratios of [$C_6H_{17}N_4R_1$]X/[resorcinol] are slightly more linear with the higher content of $R_1$ side groups. The molecular weights of the polycondensate produced, were evaluated by the measurement of their intrinsic viscosities in DMSO solutions. Intrinsic viscosities were found to vary in the range of 0.039–0.098 dl/g and depend on the type of heximinium salts used in the polycondensation reaction, the ratio [resorcinol]/[$C_6H_{12}N_4R^1X$] in the feed and the initial pH. The products with the highest degrees of polycondensation were obtained in the reaction at high heximinium salt concentration (for example for the ratio [resorcinol]/[$C_6H_{12}N_4R^1X$] of 1) and with low initial value of pH.

The reaction between resorcinol and heximinium salts can be carried out in water medium at neutral, slightly acidic or alkaline pH. The rate of the condensation polymerization process is dependent upon pH and temperature. The time the condensation polymerization reaction is carried out can vary from a few minutes to a few hours by varying the pH in the range of 4 to 8 and varying the temperature in the range of 20° to 50° C.

An important feature of the present invention is that the condensation polymerization reaction does not require the use of free formaldehyde as the latter is formed at low concentrations in situ from the hydrolysis of the heximinium salt and is quickly consumed by reaction with the $R_1NH_2$ primary amine and/or ammonia.

DETAILED DESCRIPTION OF THE INVENTION

An object of the present invention is to provide a method of treating human hair which will impart settability to the treated hair. The imparted settability allows maintaining an imparted set for a considerable length of time even under conditions of high humidity. Once set the hair will maintain its new configuration or style even after exposure to high humidities.

Another object of the prevent invention is to obtain the imparted settability by in situ condensation polymerization of heximinium salt and a resorcinol without the addition of formaldehyde.

In accordance with the present invention, hair is treated with an aqueous solution containing heximinium salt and a resorcinol. After the treating solution has had an opportunity to penetrate and saturate the hair fibers and to form the amine-resorcinol condensate polymer in situ within the hair fibers there is imparted to the hair improved settability, improved strength and improved hygroscopicity properties. Hair treated in this manner can be shampooed and reset through several cycles without losing the imparted improved settability, strength and hygroscopicity properties.

In an embodiment of the invention in order to minimize the deposition of condensation polymer on the surface of the hair, after the treating solution has had an opportunity to penetrate and saturate the hair fibers, the hair is rinsed with water to remove excess treating solution from the hair. The treating solution that has penetrated the hair fibers undergoes in situ condensation polymerization in the hair fibers to form an amine-resorcinol condensation polymer.

The aqueous treating solution is prepared by dissolving a heximinium salt and a resorcinol in water. The mole ratio of heximinium salt to resorcinol can be 1 to 5, preferably 1 to 2.5, and more preferably about 1 to 1.5.

The percent by weight of heximinium salt in the treating solution, based on salt and treating solution, can be 1 to 20, preferably 2.5 to 10, and more preferably 4 to 8% by weight. The percent by weight of resorcinol in the treating solution, based on resorcinol and treating solution, can be 5 to 50, preferably 10 to 20 and more preferably 10 to 15% by weight.

The treating solution is applied to hair at a volume ratio of treating solution to hair of 20 to 1, preferably 2 to 1, and more preferably 1 to 1. The amount of treating solution applied to the hair and the concentration of the heximinium salt and resorcinol in the treating solution are adjusted such that a weight ratio of resorcinol to hair of 1:20 to 1:1, preferably 1:10 to 1:4 and more preferably 1:10 to 1:75 is obtained.

The treating solution prior to application to the hair is adjusted to have pH 4 to 10, preferably pH 4 to 7 and more preferably pH4 to 6.

The condensation polymerization reaction can take place at a temperature of 20° to 80° C., preferably 20° to 50° C. and more preferably 20° to 40° C.

The condensation polymerization reaction time to form the desired amine-resorcinol polymer can be 0.25 to 16 hr., preferably 0.50 to 2 hr.

In treating keratin fibers, generally from the lower to the higher portions of the pH range, higher temperatures and longer treating times can be employed. In treating living hair pH 5 to 6.5, the temperatures of 30° to 45° C. and treating times of 0.5 to 2 hr are preferred. It is understood, however, that after treatment of the hair, the heximinium salt and resorcinol may continue to polymerize in situ in the hair fiber until the reaction is completed.

The heximinium salt and resorcinol condensation reaction, without the addition of a buffer, will self-adjust at the beginning of the reaction to about pH 4.5 and then steadily increase until polymer precipitation occurs at pH above 7.

To reduce the reaction medium pH to a pH of about pH 4.0 an acid buffer solution comprising potassium phthalate - HCl can be added in sufficient concentration and amount to obtain the desired pH.

In order to increase the pH to, for example, pH 6.5 to 7.5 a basic buffer solution comprising NaOH, KOH can be added in sufficient concentration and amount to obtain the desired pH.

In product application the treating solution is prepared just before the intended application. The treating solution can be prepared by mixing premeasured amounts of heximinium salt powder and a resorcinol powder in a measured amount of water or by forming a solution of the resorcinol in water and adding the heximinium salt to the aqueous resorcinol solution.

In order to facilitate application of the treating solution to living hair any cosmetically acceptable thickener may be added which is non reactive with the other constituents of the treating solution and which is stable at the pH levels and the temperature of hair treatment used. Suitable cosmetic thickeners are guar gum, Jaguar HP 60, Jaguar CMHP, etc. The thickener can be added in amounts of 0.2 to 2% by weight.

In applying the treating composition to living hair, it is preferable to first shampoo the hair with a good quality commercially available shampoo. After shampooing and rinsing, the hair may be towel dried or machine dried. The treating solution is applied in any conventional fashion in a sufficient amount to saturate the hair, for example, by dipping the hair in the treating solution, spraying, or dopping with a saturated sponge or cotton applicator.

Following the application of the treating solution to the hair, the solution should be allowed a sufficient period of time, (e.g. 0.25 to 2.0 hr, preferably 0.5 to 1 hr) to diffuse through the hair fibers and saturate and be absorbed by the hair fibers. The time required for the treating solution to saturate and be absorbed by the hair fibers will depend in part on the concentration of heximinium salt and resorcinol in the treating solution. During the period of time the treating solution is being absorbed by the hair, the hair can be wrapped in a towel or covered with a plastic cap to prevent evaporation of the treating solution. Externally applied heat from a hair dryer can be used in some situations to enhance absorption of the treating solution by the hair fibers and/or increase the rate of the formation of the condensation polymer. After the desired amount of treating solution has been absorbed by the hair, the hair can be rinsed with water to remove excess treating solution and to minimize polymer deposition on the hair surface. The treated hair is then set in the desired configuration, for example, by wrapping the hair around curlers. After setting the hair, the hair is dried and if desired can be heated by a hand held dryer or a helmet-type hair dryer to complete the condensation polymerization reaction.

As an alternative to heating the hair to complete the condensation reaction, after the absorption of the treating solution and rinsing to remove excess treating solution, the hair can be towel dried, set and allowed to remain in curlers for several hours while the condensation reaction is completed.

The following examples illustrate the preparation of the primary amine-resorcinol condensation polymer and the application of the polymer by in situ deposition in keratin fibers.

EXAMPLE 1

The condensation polymerization reaction was carried out using five heximinium salts and resorcinol. In each case 0.05 mole, (5.5 g) of resorcinol was added to 0.02 mole of the heximinium salt (5.02 to 6.24 g) in a 200 ml beaker and dissolved in 75 ml. of deionized water. The mixture was continually stirred and the reaction was carried out for 16 hours at room temperature, i.e. about 20° C. while adjusting initial pH to 4 by the addition of 25 ml of pH 4 HCl-potassium phthalate buffer solution. The condensation polymer precipitated from solution. The polymer was filtered, washed with water and dried in vacuum at room temperature to obtain light yellow or orange powders soluble in DMF and DMSO. The mole ratio of heximinium salt/resorcinol in each case was 0.02/0.05, i.e. 0.4.

The precipitated polymers were tested for solubility in DMSO (dimethysulfoxide) and DMF (dimethyl formamide) and were analyzed for primary amine and nitrogen content. The results obtained are reported in Table 1.

TABLE 1

Results of polycondensation of resorcinol (0.05 mole, 5.5 g) with heximinium salts (0.02 mole) in water at initial pH = 4 at room temperature; time of reaction was 16 hours:

| Salt | gm Salt | gm Resor. | gm Polym. | Solubility | Calc. | Fnd. |
|---|---|---|---|---|---|---|
| $[C_6H_{12}N_4C_2H_5OH]I$ | 6.22 | 5.5 | 8.7 | Hot DMSO | 7.11 | 5.52 |
| $[C_6H_{12}N_4CH_2C_6H_5]Br$ | 6.24 | 5.5 | 9.1 | DMSO, DMF | 5.77 | 6.45 |
| $[C_6H_{12}N_4CH(CH_3)_2]I$ | 6.18 | 5.5 | 8.3 | DMSO, DMF | 7.50 | 5.77 |
| $[C_6H_{12}N_4C_2H_5]I$ | 5.00 | 5.5 | 0.75 | DMSO, DMF | 7.73 | 5.39 |
| $[C_6H_{12}N_4C_2H_5]I$ | 5.90 | 5.5 | 7.9(40° C.) | | 7.73 | 5.15 |
| $[C_6H_{12}N_4CH_2(CH=CHCl)]I$ | 5.02 | 5.5 | 6.8 | DMSO, DMF | 6.22 | 5.44 |

The NMR (Nuclear Magnetic Resonance) spectra analysis of the condensate polymers obtained indicate that the primary amines $R_1NH_2$ formed during hydrolysis of the respective heximinium primary amine salts are included in the polymer structure. However, in some of the runs higher yields of polymer were obtained than the calculated yields. For example, 0.05 mole resorcinol and 0.02 mole of $[C_6H_{12}N_4C_2H_5OH]I$ would be expected to yield 0.05 mole of polymer, i.e. 6.8 g whereas the actual yield of polymer was 8.7 g, and expected nitrogen content was 7.11 percent, whereas only 5.52 percent nitrogen was found.

The higher yield of polymer and the lower then expected amount of nitrogen content found in the polymer indicate that the ammonia and formaldehyde released on hydrolysis of the heximinium salt react to form an intermediate product ($CH=NH_2$) which then reacts with the resorcinol to form additional polymer. This is believed to result in the formation of highly branched resorcinol polymer structure, since resorcinol and ammonia each have three active reaction sites. Further, under the above Table 1 reaction conditions, it was found that resorcinol does not react with formaldehyde to form a condensation product. In addition an attempt to carry out the condensation polymerization reaction under reaction conditions similar to those of Table 1 using 0.02 mole (2.8 g) hexamine (hexamethylenetetramine) and 0.02 mole resorcinol (2.2 g) resulted in obtaining very little polymer (0.15 g). This is believed to be due to the very low rate of hydrolysis of hexamine compared with the heximinium salts.

EXAMPLE 2

In order to determine the effect on polymer yield of the ratio of heximinium salt/resorcinol used to carry out the condensation polymerization reaction several polymerization reactions were carried out using varying amounts of resorcinol. In each case 0.02 mole of 1-(3-chloro-2-propenyl) heximinium chloride was used and the amount of resorcinol was varied between 0.004 to 0.1 mole. The heximinium salt and resorcinol were dissolved in 75 ml of deionized water placed in a 200 ml beaker. The condensation polymerization reactions were carried out for 16 hours at room temperature which adjusting the initial pH to 4 by the addition 25 ml of HCl-potassium phthalate buffer solution. The mole ratio of heximinium salt/resorcinol was varied between 5.0 to 0.2. The polymers as they formed precipitated from solution, were filtered, washed with water and dried in a vacuum at room temperature. The precipitated polymers were as before analyzed for nitrogen content. The results obtained are reported in Table 2.

TABLE 2

Effect of the ratio $[(C_6H_{12}N_4CH_2CH=CHCl)Cl]/$ [resorcinol] on the yield of the polycondensate; temp. 25° C.; reaction time = 16 hrs:

| Salt/Resorcinol | gm Salt | gm Resorcinol | gm Polymer | % N Calc. | % N Found |
|---|---|---|---|---|---|
| 5 | 5.02 | 0.44 | 0.9 | 6.22 | 7.17 |
| 2 | " | 1.1 | 0.82 | 6.22 | 6.39 |
| 1 | " | 2.2 | 3.45 | 6.22 | 6.16 |
| 0.5 | " | 4.4 | 6.8 | 6.22 | 5.44 |
| 0.2 | " | 11.0 | 12.1 | 6.22 | 4.93 |

A nitrogen analysis of the polymers was carried out and indicated that the polymer obtained at the high salt/resorcinol ratios contain primarily secondary amine end groups whereas the polymer obtained at the low salt/resorcinol ratios contain primarily resorcinol end groups.

EXAMPLE 3

The effect of pH of the reaction medium on the yield of polymer was determined by carrying out several condensation polymer reactions at various initial pH's. The condensation polymerization reaction was carried out by dissolving 0.02 mole of 1-(3-chloro-2-propenyl)

hexaminium chloride, (5.0 gm) and 0.1 mole of resorcinol (11 gm) in 75 ml of water in a 200 ml beaker. The reaction was carried out at room temperature for 0.5 to 4.0 hours while varying the pH between pH 3 and 7.3 by the addition of 25 ml appropriate buffer solutions. The polymers precipitated from solution, were filtered, washed with water and dried in a vacuum at room temperature (20° C.). The results obtained are reported in Table 3.

TABLE 3

Polycondensation of 1-(3-chloro-2-propenyl) heximinium chloride - resorcinol at various pH in water at room temperature:

| ph | gm Salt | gm Resorcinol | gm Polymer | Time |
|---|---|---|---|---|
| 3 | 5.02 | 11.0 | 12.6 | 4 hrs. |
| 4.2 | " | " | 13.6 | — |
| 6.2 | " | " | 13.3 | — |
| 7.3 | " | " | 12.9 | 0.5 hr. |

Polycondensation of 1-(3-chloro-2-propenyl) heximinium chloride - resorcinol at various pH in water at room temperature:

The above data show that the rate of polymer formation increases with the pH.

EXAMPLE 4

The effect of reaction temperature on the condensation polymerization reaction was determined by carrying out the reaction at temperatures ranging from 25° C. to 80° C.

The condensation polymerization reaction was carried out by dissolving 0.02 mole of 1-(3-chloro-2-propenyl) heximinium chloride (5.02 gm) and 0.1 mole of resorcinol (11 gm) in 75 ml of water in a 200 ml beaker. The ratio of salt to resorcinol was 0.2. The initial pH of the reaction was adjusted to 4 by the addition of 25 ml of HCl potassium phthalate buffer solution. The polymer as they formed precipitated from solution, were filtered, washed and dried in a vacuum at room temperature. The precipitated polymers were checked for solubility in DMF and DMSO. The results obtained are reported in Table 4.

TABLE 4

Polycondensation of 1-(3-chloro-2-propenyl) heximinium chloride - resorcinol at various temperatures:

| Temp. | gm Salt | gm Resorcinol | gm Polymer | Time | Solubility |
|---|---|---|---|---|---|
| 20° C. | 5.02 | 11.0 | 12.6 | 4 hrs. | Sol. Cold DMF, DMSO |
| 40° C. | " | " | 13.7 | 4 hrs. | Sol. Warm DMF, DMSO |
| 80° C. | " | " | 14.1 | 0.5 hr. | Ins. DMF, Swells DMSO |

The increase in reaction temperature decreased the solubility of the polymer obtained in both DMF and DMSO and accelerated the reaction such that polymer precipitates were obtained sooner.

EXAMPLE 5

The effect of pH of the reaction medium and reaction time on the amount of polymer absorbed by hair fibers and the hygroscopicity of the treated hair fibers was determined by carrying out several condensation polymer reactions at pH 4.5 and 7.5 and at reaction times of 0.5 to 24 hours. The condensation polymerization reaction was carried out by dissolving 0.02 mole of 1-(3-chloro-2-propenyl) heximinium chloride (5.02 gm) and 0.1 mole of resorcinol (11 gm) in 75 ml of water in a 200 ml beaker. 4 gms to 5 gms of hair fibers (polycondensation mixture was in large excess) were added to the reaction medium. The reaction was carried out at 25° C. The reaction mixture self adjusted to initial pH of 4.5 without the addition of a buffer. The initial pH of 7.5 was adjusted by the addition of 25 ml of KOH solution. The polymers were formed in situ in the hair fibers and on the hair surface. The fibers containing absorbed polymer were filtered, washed with water and dried in a vacuum at room temperature. The dried fibers were placed in a controlled environment for 24 hours at 70° F. and 65% to determine water uptake.

The results obtained are reported in Table 5.

TABLE 5

Polymer uptake and hygroscopicity of hair fibers treated with polycondensate 1-(3-chloro-2-propenyl) heximinium chloride - resorcinol; [salt]/[resorcinol] = 0.2, [resorcinol] = 0.1 M: temp. = 25° C.:

| Sample | pH | Time Hrs. | % Polymer Deposition | % Water Uptake 65% RH, 70° F. |
|---|---|---|---|---|
| 1 | 4.5 | 2 | 5.97 | 7.48 |
| 2 | 4.5 | 4 | 8.5 | 6.96 |
| 3 | 4.5 | 6 | 11.42 | 7.15 |
| 4 | 4.5 | 8 | 13.94 | 6.94 |
| 5 | 4.5 | 24 | 17.68 | 7.01 |
| 6 | 7.5 | 0.5 | 4.87 | 8.77 |
| 7 | 7.5 | 1 | 6.83 | 8.29 |
| 8 | 7.5 | 2 | 8.89 | 8.14 |
| 9 | 7.5 | 4 | 12.0 | 8.46 |
| 10 | 7.5 | 24 | 16.11 | 8.51 |
| Untreated Hair Fibers | | | 0.00 | 12.5 |

The data obtained show that the rate and amount of polymer deposition in the hair fibers is strongly influenced by the pH of the reaction medium, i.e. at the higher pH of 7.5 the polymerization reaction rate is faster and more polymer is deposited in the hair fibers. The water uptake data show that the hygroscopicity imparted to the hair fibers is greater at the pH of 7.5 reaction conditions. For example, the samples 6–10 carried out at pH 7.5 exhibit an average 8.43% water uptake as compared to samples 1–5 average 7.11% water uptake.

The treated sample 2 (pH 4.5, 4 hrs) hair fibers were analyzed and were found to have a smooth and uniformly distributed thin about 0.2 micron surface coating of polymer. The hair fibers were about 70 microns in diameter and were about the same density as the polymer. The analysis showed that about 1.2% of the 8.5% polymer uptake of the hair fiber was deposited on the outer surface of the fiber and about 7.3% of the polymer uptake was precipitated in situ inside of the hair fiber. The treated sample 7 (pH 7.5, 1 hr) showed a similar polymer deposit pattern to that of sample 2. The treated hair fibers at longer times, e.g. sample 5 (pH 4.5, 24 hrs) and sample 10 (pH 7.5, 24 hrs) showed areas of relatively thick deposit layers of polymer distributed at random on the hair surface.

EXAMPLE 6

The effect of the ratio of the amount of resorcinol to the amount of hair treated on the amount of condensation polymer absorbed by the hair fiber was determined by carrying out the condensation polymerization reaction in the presence of varying amounts of resorcinol while using the same amount of hair fiber in the reaction medium. The polymer uptake of the hair fiber and the imparted hygroscopicity were in each case measured.

In each case the reaction temperature was maintained at 37° C. and the reaction time 2.5 hours. PH was self-adjusted to initial value of 4.5.

The condensation polymerization reaction medium was prepared by dissolving 0.1 mole of resorcinol (11 gm) and 0.2 mole of 1-(3-chloro-2-propenyl) hexaminium chloride (5.02 gm) in 100 ml of water. One gram of hair fiber was placed in a 200 ml beaker and a sufficient amount of the reaction medium was added to the hair fiber with stirring to obtain the desired weight ratio of resorcinol to hair. After each run the hair and polymer were removed and dried and placed in a controlled environment for 24 hrs at 70° C. and 65% RH to determine water uptake.

The results obtained are reported in Table 6.

TABLE 6

Polymer uptake and hygroscopicity of hair fibers treated with polycondensate 1-(3-chloro-2-propenyl) heximinium chloride - resorcinol at various hair/liguor ratios; [salt]/[resorcinol] = 0.2, [resorcinol] = 0.1 M, temp. 37° C., time = 2.5 hrs; liquor ratios expressed as the amount of resorcinol in grains applied to 1 g of hair:

| ml of Treating Solution | gm Salt | gm Resor | gm Hair | gm Ratio Resor/Hair | % Polymer Deposition | % Water Uptake 65% RH, 70° F. |
|---|---|---|---|---|---|---|
| 1.13 | 0.0518 | 0.1134 | 1.0 | 0.1134 | 6.58 | 10.15 |
| 2.43 | 0.1109 | 0.2429 | 1.0 | 0.2429 | 14.48 | 11.24 |
| 5.00 | 0.2284 | 0.5002 | 1.0 | 0.5002 | 12.03 | 9.39 |
| 5.97 | 0.2227 | 0.5973 | 1.0 | 0.5973 | 16.29 | 9.55 |
| 14.44 | 0.6593 | 1.4438 | 1.0 | 1.4438 | 17.49 | 8.33 |
| — | — | — | 1.0 | Untried Hair | 0.00 | 13.50 |

The sample treated with the smallest amount of condensate polymer (resorcinol/hair of 0.1134) exhibited no external deposition of polymer. The increase of resorcinol/hair ratio led to an increasingly thicker layer of polymer deposition on the hair fiber surface.

The data obtained also show that as the amount of polymer deposition increased the hygroscopicity of the treated hair decreased.

EXAMPLE 7

The effect of pH of the reaction medium on the deposition of condensate polymer in virgin hair fibers was determined by carrying out several condensation polymer reactions in the presence of hair fibers at 37° C. and at pH ranges of about pH 5.0 to 10.0. The condensation polymerization reaction was carried out by dissolving 0.02M of 1-(3-chloro-2-propenyl) heximinium chloride (5.02 gm) and 0.1M resorcinol (11 gm) in 75 ml of water in a 200 ml beaker. The initial pH of the polycondensation mixture was adjusted with HCl or NaOH, and the reaction was carried out for 0.5 hrs. at 37° C.

The results obtained are reported in Table 7.

TABLE 7

Effect of pH on the amount of deposition of the polycondensate 1-(3-chloro-2-propenyl) heximinium chloride - resorcinol in hair fibers:

| Temp | pH | gm Salt | gm Resorcinol | Liquor/Hair | % Polymer Deposition |
|---|---|---|---|---|---|
| 37° C. | 5.5 | 5 g/100 ml | 11 g/100 ml | 2 | 6.8 |
| 37° C. | 6.0 | 5 g/100 ml | 11 g/100 ml | 2 | 7.0 |
| 37° C. | 6.5 | 5 g/100 ml | 11 g/100 ml | 2 | 7.3 |
| 37° C. | 7.0 | 5 g/100 ml | 11 g/100 ml | 2 | 8.6 |
| 37° C. | 7.5 | 5 g/100 ml | 11 g/100 ml | 2 | 8.8 |
| 37° C. | 8.5 | 5 g/100 ml | 11 g/100 ml | 2 | 10.4 |
| 37° C. | 9.0 | 5 g/100 ml | 11 g/100 ml | 2 | 8.7 |
| 37° C. | 9.5 | 5 g/100 ml | 11 g/100 ml | 2 | 5.8 |

The data show in treating virgin hair that at 0.5 hour reaction time the percent polymer deposition or uptake by the hair increases with the increase in pH until an alkaline pH is reached after which continued increase in pH results in a decrease in polymer uptake. At pH values higher than about pH 8, the condensation reaction proceeds at so high a rate that the resorcinol monomer does not have sufficient time to penetrate inside the hair structure and substantial amounts of the polymer is formed outside on the surface of the hair fiber.

EXAMPLE 8

The effect of pH on the reaction medium on the deposition of condensate polymer in damaged hair fibers was determined by carrying out several condensation polymer reactions in the presence of damaged hair fibers at 37° C. and at pH ranges of about pH 5.0 to 9.0.

The condensation polymerization reaction was carried out by dissolving 0.02 M of 1-(3-chloro-2-propenyl) heximinium chloride (5.02 gm) and 0.1 M of resorcinol (11 gm) in 75 ml of water in a 200 ml beaker to which was added 25 ml of pH 5–8 buffer solution to adjust the desired initial pH. This solution was used to treat the fibers for 0.5 hour at liquor/hair ratio of 2 and at 37° C. The results obtained are reported in Table 8.

TABLE 8

| 1-(3-chloro-2-propenyl) heximinium chloride | | | | | |
|---|---|---|---|---|---|
| Temp | pH | gm Salt | gm Resorcinol | Liquor/Hair | % Polymer Deposition |
| 37° C. | 5.5 | 5 g/100 ml | 11 g/100 ml | 2 | 5.8 |
| 37° C. | 6.0 | 5 g/100 ml | 11 g/100 ml | 2 | 5.7 |
| 37° C. | 6.5 | 5 g/100 ml | 11 g/100 ml | 2 | 5.9 |
| 37° C. | 7.0 | 5 g/100 ml | 11 g/100 ml | 2 | 6.3 |
| 37° C. | 7.5 | 5 g/100 ml | 11 g/100 ml | 2 | 8.5 |
| 37° C. | 8.0 | 5 g/100 ml | 11 g/100 ml | 2 | 8.2 |
| 37° C. | 8.5 | 5 g/100 ml | 11 g/100 ml | 2 | 6.5 |

The data shows in treating damaged hair that at 0.5 hour reaction time the percent polymer deposition or uptake by the hair increases with the increase in pH until an alkaline pH is reached after which continued increase in pH results in a decrease in polymer uptake. At pH values higher than about pH 8, the condensation reaction proceeds at so high a rate that the resorcinol monomer does not have sufficient time to penetrate inside the hair structure and substantial amount of the polymer is formed outside and/or on the surface of the hair fiber.

It will be understood that various changes and modifications may be made in the invention, and that the scope thereof is not to be limited except as set forth in the following claims.

What is claimed is:

1. A composition for decreasing hair hygroscopicity and thus imparting improved settability to keratin fibers, which comprises an aqueous solution containing a sufficient amount of heximinium salt and a sufficient amount of a resorcinol to form in situ in the keratin fibers a keratin fiber setting amount of a condensation polymer derived from said heximinium salt and said resorcinol.

2. The composition of claim 1 wherein the heximinium salt has the formula [C$_6$H$_{12}$N$_4$R$_1$]X and the resorcinol has the formula

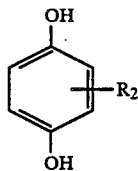

R$_1$ is a substituted or unsubstituted straight or branched chain alkyl, aryl, aralkyl or olefinic group containing up to 18 carbon atoms, X is a halide, and R$_2$ is hydrogen or alkyl having 1 to 12 carbon atoms.

3. A composition according to claim 2 wherein R$_1$ contains from 2 to 18 carbon atoms.

4. The composition of claim 1 wherein said heximinium salt decomposes in the aqueous solution to form decomposition products R$_1$NH$_2$, NH$_3$ and CH$_2$O, which decomposition products form intermediate products CH$_2$=NHR and CH$_2$=NH$_2$ which react with the resorcinol to form the condensation polymer wherein R$_1$ is a substituted or unsubstituted straight or branched chain alkyl, aryl, aralkyl or olefinic group containing up to 18 carbon atoms.

5. The composition of claim 1 wherein the heximinium salt is a member selected from the group consisting of
[C$_6$H$_{12}$N$_4$C$_2$H$_5$]I, [C$_6$H$_{12}$N$_4$CH(CH$_3$)$_2$]I,
[C$_6$H$_{12}$N$_4$C$_2$H$_5$OH]I, [C$_6$H$_{12}$N$_4$CH$_2$C$_6$H$_5$]Br,
[C$_6$H$_{12}$N$_4$CH=CHCH$_2$Cl]Cl, [C$_6$H$_{12}$N$_4$C$_{14}$H$_{29}$]I,
[C$_6$H$_{12}$N$_4$C$_{18}$H$_{37}$]Br and [C$_6$H$_{12}$N$_4$CH$_2$CH=CH$_2$]Br
and the resorcinol is a member selected from the group consisting of resorcinol and 2-methyl resorcinol.

6. The composition of claim 1 wherein the mole ratio of heximinium salt and resorcinol in the aqueous solution is 1:5 to 1:1.

7. The composition of claim 1 wherein the aqueous solution has an initial pH in the range of 4 to 8.

8. The composition of claim 1 for imparting improved settability to hair comprising 1 to 20% by weight hemiminium salt and 5 to 50% by weight resorcinol.

9. A novel condensation polymer comprising the reaction product of heximinium salt and resorcinol.

10. The condensation polymer of claim 9, wherein the heximinium salt has the formula [C$_6$H$_{12}$N$_4$R$_1$]X and the resorcinol has the formula

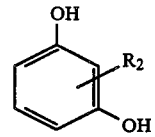

where R$_1$ is a substituted or unsubstituted straight or branched chain alkyl, aryl, aralky or olefinic group containing up to 18 carbon atoms, X is a halide and R$_2$ is hydrogen or a alkyl having 1 to 12 carbon atoms.

11. The condensation polymer of claim 9 wherein the polymer is formed in an aqueous solution and the heximinium salt decomposes in the aqueous solution to form decomposition products R$_1$NH$_2$, NH$_3$ and CH$_2$O, which decomposition products form intermediate products CH$_2$=NHR$_1$ and CH$_2$=NH$_2$ which react with the resorcinol to form the condensation polymer wherein R$_1$ is a substituted or unsubstituted straight or branched chain, alkyl, aryl aralkyl or olefinic group containing up to 18 carbon atoms.

12. The condensation polymer of claim 9 wherein the heximinium salt is a member selected from the group consisting
of [C$_6$H$_{12}$N$_4$C$_2$H$_5$]I, [C$_6$H$_{12}$N$_4$CH(CH$_3$)$_2$]I,
[C$_6$H$_{12}$N$_4$C$_2$H$_5$OH]I, [C$_6$H$_{12}$N$_4$CH$_2$C$_6$H$_5$]Br,
[C$_6$H$_{12}$N$_4$CH=CHCH$_2$Cl]Cl, [C$_6$H$_{12}$N$_4$C$_{19}$H$_{29}$]I,
C$_6$H$_{12}$N$_4$C$_{18}$H$_{37}$]Br and [C$_6$H$_{12}$N$_4$CH=CH$_2$]Br, and the resorcinol is a member selected from the group consisting of resorcinol and 2-methyl resorcinol.

13. The condensation polymer of claim 9 wherein the mole ratio of the heximinium salt and resorcinol reactant is 1:5 to 1:1.

14. The condensation polymer of claim 9 wherein the heximinium salt and the resorcinol reaction is carried out in an aqueous reaction solution at a pH in the range of 4 to 8.

* * * * *